United States Patent [19]

Murphy, Jr. et al.

[11] Patent Number: 4,606,891
[45] Date of Patent: Aug. 19, 1986

[54] ELECTRODE HOLDER USEFUL IN A CORROSION TESTING DEVICE

[75] Inventors: Robert J. Murphy, Jr., Bellaire; Dale E. Jamison, Humble, both of Tex.

[73] Assignee: NL Industries, Inc., New York, N.Y.

[21] Appl. No.: 625,771

[22] Filed: Jun. 28, 1984

[51] Int. Cl.⁴ .................. G01N 17/00; B25B 1/20; B01L 9/00; C25D 17/08
[52] U.S. Cl. .................................. 422/53; 73/859; 204/297 R; 204/297 W; 269/43; 269/254 CS; 324/158 F; 422/99
[58] Field of Search .................. 422/53, 99; 436/6; 73/856, 855, 859, 860, 86; 269/43, 254 CS, 146; 324/158 F, 65 CR; 204/404, 297 R, 297 W, 285, 286; 219/144

[56] References Cited

U.S. PATENT DOCUMENTS

| | | | |
|---|---|---|---|
| 1,242,610 | 10/1917 | Sindelar | 269/254 CS |
| 1,906,378 | 5/1933 | Howard | 204/297 R |
| 2,133,372 | 10/1938 | Barton | 269/254 CS |
| 2,352,857 | 7/1944 | Nachemov | 269/254 CS |
| 2,523,973 | 9/1950 | Snyder | 204/297 R |
| 2,664,744 | 1/1954 | Bihartz et al. | 422/53 |
| 3,666,159 | 5/1972 | Watson | 269/43 |
| 3,685,969 | 8/1972 | Young, III | 422/53 |
| 3,801,796 | 4/1974 | Busch | 269/43 |
| 4,074,422 | 2/1978 | Borjesson et al. | 269/43 |
| 4,102,769 | 7/1978 | Seyl | 73/86 |
| 4,326,703 | 4/1982 | Marley | 269/287 |

FOREIGN PATENT DOCUMENTS 2544634  4/1977 Fed. Rep. of Germany ... 204/297 R

Primary Examiner—S. Leon Bashore
Assistant Examiner—K. M. Hastings
Attorney, Agent, or Firm—Browning, Bushman, Zamecki & Anderson

[57] ABSTRACT

The present invention is directed to an apparatus and method for holding one or more test electrodes of precisely known exposed surface area. The present invention is particularly useful in a device for determining the corrosion properties of the materials from which the test electrodes have been formed. The present invention relates to a device and method for holding the described electrodes wherein the exposed surface area of the electrodes is only infinitesimally decreased. Further, in the present invention the exposed, electrically conductive surface area of the contact devices is small relative to the test electrode surface area. The holder of the present invention conveniently comprises a device for contacting and engaging each test electrode at two point contacts infinitesimally small in relation to the exposed surface area of the electrodes.

5 Claims, 4 Drawing Figures

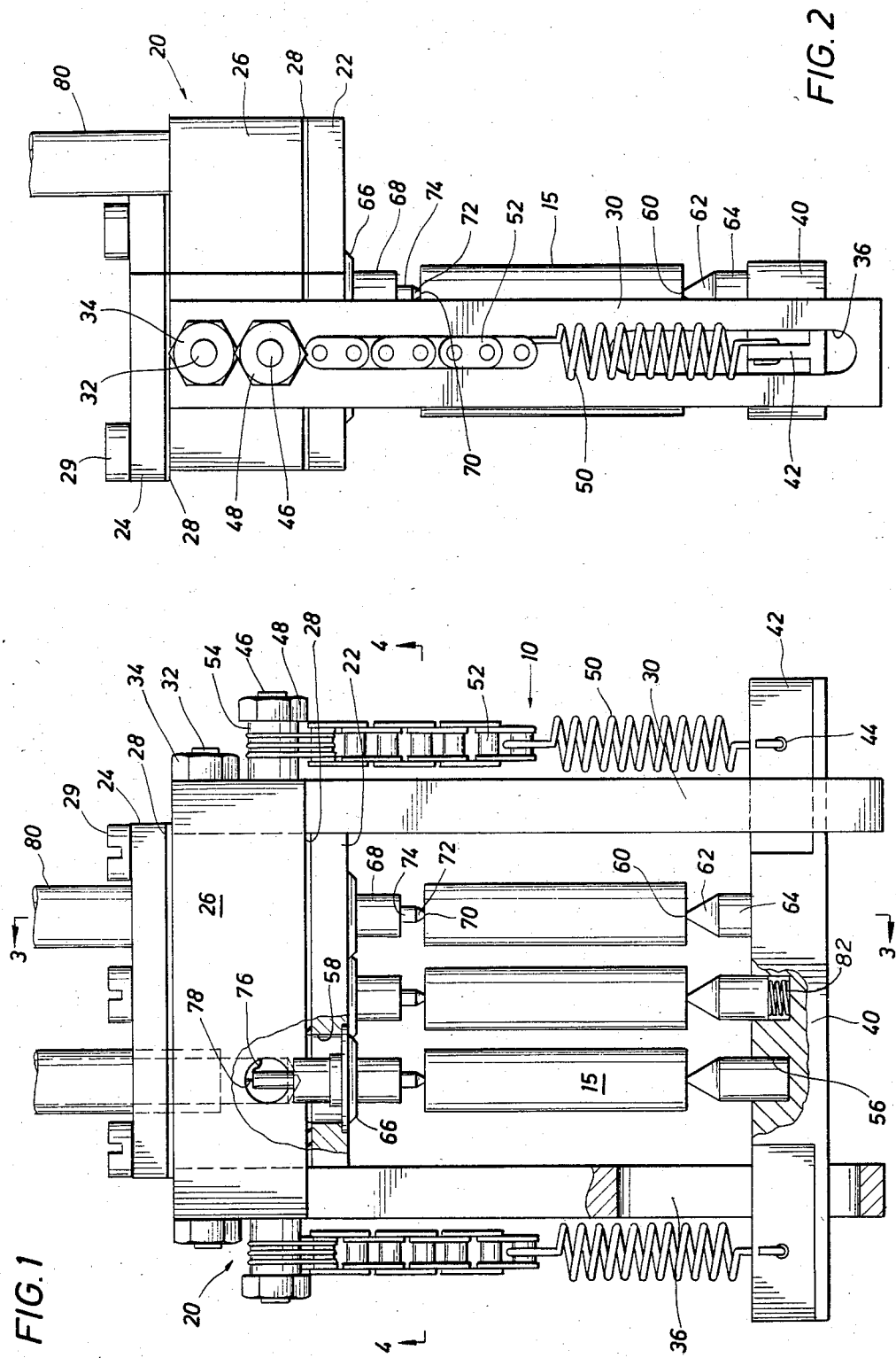

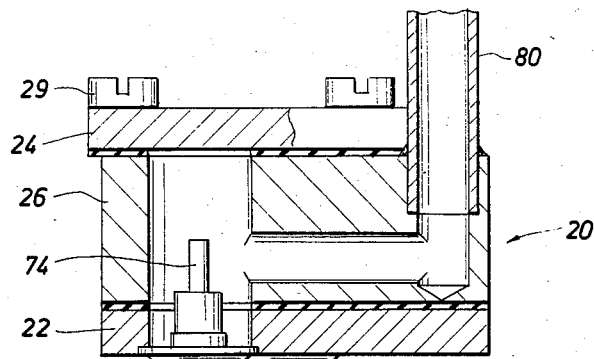
FIG. 3
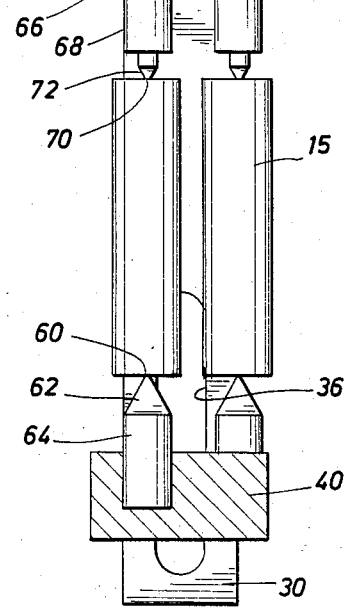
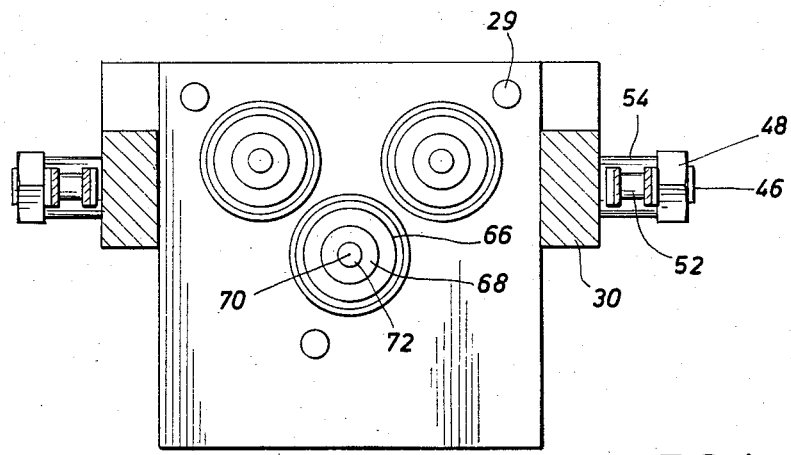
FIG. 4

ELECTRODE HOLDER USEFUL IN A CORROSION TESTING DEVICE

Statement of Government Rights

The government of the United States of America has rights in this invention pursuant to Government Contract No. DE-AC-04-77ET 27144 awarded by the U.S. Department of Energy.

BACKGROUND OF THE INVENTION

1. Field of the Invention

The present invention generally relates to an apparatus and method generally useful for holding one or more electrodes of precisely known exposed surface area. The present invention is particularly useful in a device for determining under a variety of conditions the corrosion properties of the material from which the electrode has been formed. More particularly, the present invention relates to a device for holding the described electrodes by a means which only infinitesimally decreases the exposed surface area of the electrodes and which is characterized by an exposed electrically conductive surface area which is small relative to the surface area of the test electrode.

2. Description of the Background

It is often desirable to determine the corrosion characteristics of materials under a variety of conditions simulating the working environment where devices constructed of the materials are projected to be employed. It will be appreciated by those skilled in the art that these tests are conveniently conducted on test electrodes formed of the materials. In conducting these tests, the test electrodes are exposed to conditions simulating the projected working environment or often to conditions simulating the most severe conditions to which the materials are expected to be exposed. For example, corrosion tests of materials used to construct or in connection with downhole devices are preferably performed in a simulated downhole environment. These tests are typically conducted in the presence of drilling muds and at extremely high temperatures and pressures. In fact, temperatures approaching 450° F. and pressures in excess of 10,000 psi are not uncommon. Further, these tests are often performed in the presence of corrosive fluids, e.g., hydrogen sulfide, which might be encountered in drilling operations.

The corrosion test electrodes employed for these determinations are often electrically isolated from their environment. Alternatively, a working voltage is applied to the test electrodes. In order to correctly analyze the effects of corrosion on a test electrode, including calculation of the corrosion rate under various conditions of temperature, pressure and the like, it is necessary that the surface area of the test electrode exposed to the test conditions be precisely known. These test methods have required the production of electrodes of precisely known exposed surface area. Typically, these electrodes are manufactured in the shape of rods. These rods are maintained in the test device by insertion into appropriate chucks or bores which have significantly and non-reproducibly altered the exposed surface area. The non-reproducibility of the surface area remaining exposed in these devices has reduced the accuracy of corrosion effect data obtained by these methods.

Accordingly, there has been a long felt but unfulfilled need within the testing industry for a corrosion test electrode holder which securely engages a plurality of test electrodes in a manner resulting in the engaged electrodes having precisely known exposed surface areas.

SUMMARY OF THE INVENTION

The present invention provides a new and improved holder useful in corrosion testing of materials in the form of electrodes of precisely known exposed surface area. The disclosed device and method comprises contacting one or more of the test electrodes by an engaging means which only infinitesimally decreases the exposed surface area of the electrode and which has an electrically conductive surface area small relative to the test electrode surface area and biasing the engaging means to an engaged position. The present invention provides a holder for securely and firmly engaging test electrodes of precisely known exposed surface area at point contacts which result in essentially no change in the exposed surface area.

A holder in accord with the present invention conveniently comprises first and second electrode mounting plates. Mounted on these plates are a plurality of pairs of electrode contacting means. The first mounting plate has thereon the first member of each pair and the second mounting plate has thereon the second member of each pair. A convenient and reliable biasing means is a simple tension spring. Further, a spring and chain arrangement provides a biasing means conveniently adjustable to a variety of strengths.

Each of the electrode contacting means comprises a point for contacting an electrode on an infinitesimally small surface area relative to the precisely known surface area of the electrode. An engaging means including a conical portion ending in a contacting point is presently preferred. It is contemplated that some or all of the contacting members of the present invention are comprised of a high resistance, electrically non-conductive material such as glass or ceramic. However, in an alternative embodiment, one or more of the first contacting members is comprised of a low resistance, electrically conductive material. Futher, this alternative embodiment includes means for applying a voltage across the electrodes. A plurality of these members are arranged in electrical contact to conduct a current which is naturally generated between electrodes or a voltage is applied to one or more of the electrodes from an outside source.

The device and method of the present invention solve the long felt but unfulfilled need for a test electrode holder for corrosion testing sample electrodes of precisely known surface areas. The device and method of the present invention essentially do not alter the exposed surface area of the sample electrodes of precisely known surface area. This device and method permit corrosion tests to be performed precisely and accurately. These and other meritorious features and advantages of the present invention will be more fully appreciated from the following detailed description and claims.

BRIEF DESCRIPTION OF THE DRAWINGS

Other features and intended advantages of the present invention will be more readily apparent by the references to the following detailed description in connection with the accompanying drawings, wherein:

FIG. 1 is a front illustration in partial cross section of a test electrode holder in accord with the present invention;

FIG. 2 is a side illustration of a test electrode holder in accord with the present invention;

FIG. 3 is a vertical cross-sectional illustration of a test electrode holder in accord with the present invention through the plane 3—3 of FIG. 1;

FIG. 4 is a horizontal cross-sectional illustration of a test electrode holder in accord with the present invention throught the plane 4—4 of FIG. 1.

While the invention will be described in connection with the presently preferred embodiment, it will be understood that it is not intended to limit the invention to this embodiment. On the contrary, it is intended to cover all alternatives, modifications and equivalents as may be included in the spirit of the invention as defined in the appended claims.

DETAILED DESCRIPTION OF THE PREFERRED EMBODIMENT

FIGS. 1–4 of the drawings illustrate a presently preferred embodiment of a point contact sample electrode holder in accord with the present invention. This system is particularly useful in the determination of corrosion characteristics, including corrosion rate of the material from which the test electrode has been formed. These tests are generally performed under conditions simulating the typical use environment of devices constructed from the test material or under the most severe conditions expected to be encountered by these devices.

A presently preferred embodiment of a test electrode holder 10 in accord with the present invention is illustrated in FIGS. 1–4. The illustrated electrode holder 10 is constructed to conveniently and compactly engage up to three test electrodes 15 for simultaneous corrosion testing. The electrode holder 10 comprises an electrode mounting block 20. First mounting block 20 comprises a first electrode mounting plate 22 to which the first contacting members are affixed, a central block 26 through which electrical contacts are made and to which the biasing means is attached and a top plate 24. The top and bottom plates 24 and 22 are conveniently affixed to the middle block 26 by threaded screws 29 through tapped bores therein or by any other conventional means. Fluid in which the holder may be immersed is prevented from entering the interior of block 20 where electrical connections may be affected by a pair of sealing gaskets 28. These gaskets must be able to withstand the severe test conditions in which the holder will be employed.

This preferred embodiment of the present invention further comprises a second mounting plate 40 to which the second contact members are affixed. Mounting plate 40 is conveniently and adjustably affixed in cooperation with mounting plate 22 by a plurality of mounting arms 30. Mounting arms 30 are attached to block 26 by any conventional means, such as by insertion of threaded studs 32 extending from block 26 through appropriate slots or bores (not shown) in arms 30. Nuts 34 securely attach the arms 30. Each arm 30 is characterized by an elongate slot 36 through which a narrowed portion 42 of the plate 40 extends. Appropriate selection of the length of the arms 30 together with the size and location of the slots 36 permits construction of a holder capable of testing sample electrodes of any desired length.

A convenient and adjustable means for biasing the mounting plates 22 and 40 toward one another comprises a plurality of springs 50 attached at one end to the plate 40 as through bores 44 and attached at the other end to the mounting block 20. Biasing means having an adjustable strength is conveniently produced by employing chains 52 attached to sleeves 55 about threaded studs 46 and secured in place by nuts 48. The strength of the biasing means is readily adjusted by appropriately choosing springs 50 and further adjusted by affixing one end of the springs 50 to an appropriate link of the chains 52.

Affixed to the second mounting plate 40 is a plurality of contact means. For example, cylindrical insulators 64 terminating in cones 62 having contact points 60 are conveniently inserted within the bores 56 in the mounting plate 40. The insulators 64 comprise a high resistance, electrically non-conductive material. Illustrative materials are glass, ceramic and the like. Although the described contact means is presently preferred, those skilled in the art will appreciate that the present invention contemplates the use of any contact means having single contact points 60 which only infinitesimally decrease the precisely known surface area of the test electrodes 15.

The presently preferred embodiment further comprises a plurality of contact members 74 also terminating in cones 72 having single point contacts 70. In one embodiment, the contact members 74 are comprised of a low resistance, electrically conductive material having an exposed surface area small relative to the surface area of the test electrode 15. The ratio of the exposed surface area of the member 74 to the exposed surface area of the test electrode 15 is preferably 0.01 or less, and ideally approaches zero. Illustrative materials include the typical electrical conductors, notably copper and silver. In an alternative embodiment, one or more of the contact members 74 in an electrode holder 10 in accord with the present invention is comprised of a high resistance, electrically non-conductive material described above. The contact members 74 are securely held within insulators 68 which in turn are securely held within holders 66 in bores 58 through the mounting plate 22. In one embodiment of the present invention, a plurality of the contact members 74 are placed in electrical contact with conductors 76 to establish natural electromotive cells between test electrodes. Alternatively, a voltage is applied to one or more test electrodes as from an external power source (not shown) applied through an electrical conductor 78. One or more tubular conduits 80 are conveniently affixed to sample electrode holder 10. The conduits 80 conveniently provide means for suspending the electrode holder 10 within the test environment and provide means shielded from the environment through which an electrical conductor 78 is passed.

It will be appreciated by those skilled in the art that all of the exposed surfaces of a device in accord with the present invention, e.g., block 26, plates 22, 24 and 40, arms 30, conduits 80, chains 52, springs 50 and the various minor parts are constructed of materials which will not be affected by the test environment. The material of choice is generally stainless steel.

The method of the present invention comprises contacting one or more test electrodes of precisely known exposed surface area by engaging means which only infinitesimally decrease the exposed surface area of the contacted electrodes and biasing the engaging means to an engaged position to hold the electrodes. This method is conveniently and easily performed employing a device in accord with the present invention, e.g., the device described above. It is believed that the description of the above preferred embodiment of the present invention clearly conveys the method of the present invention in a manner appreciated by those skilled in the art. However, in summary, the method of the present invention is conveniently performed employing the electrode holder 10 described above. The method comprises engaging one or more test electrodes 15 between point contacts 60, 70 of a pair of contacting members 64 and 74 securely affixed to mounting plates 40 and 22. Test electrodes 15 are securely engaged and held in place by the force of springs 50 urging the first plate 40 toward the second plate 22. The strength of this force is conveniently adjusted by attaching the springs 50 to any desired link of the chains 52. A voltage may be applied to one or more of the electrodes 15 as through the conductors 76 or 78 as described above when one contact member 74 for each electrode is an electrical conductor.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described apparatus and method may be made without departing from the scope and spirit of the invention. For example, the contact members 64 and 74 may be constructed in any desirable shape or configuration restrained only by the rstriction that the contact points 60 and 70 be infinitesimally small in relation to the exposed surface area of the test electrodes 15. Further, any means for collectively or individually biasing each pair of contact members 64, 74 toward one another may be employed. For example, one or both of each pair of contact members 64, 74 may be individually spring biased by spring 82 into secure engagement with a test electrode 15. Therefore, the invention is not restricted to the particular form of construction and method illustrated and described, but covers all modifications which may fall within the scope of the following claims.

It is Applicants' intention in the following claims to cover such modifications and variations as fall within the true spirit and scope of the invention.

What is claimed is:

1. A corrosion testing rack for testing a plurality of elongated, cylindrical electrodes of precisely known surface area constructed of a material whose corrosion characteristics are to be determined, comprising:
   a first electrode mounting plate;
   a plurality of first contact means, said first contact means disposed on said first mounting plate and including a conical portion for point contact with a first end of said cylindrical electrodes;
   a second electrode mounting plate;
   a plurality of insulating second contact means, said second contact means disposed on said second mounting plate in a configuration for cooperation with said first contact means and including a conical portion for point contact with a second end of said cylindrical electrodes;
   two guides extending from opposite ends of said second mounting plate;
   two spacing arms rigidly attached to said first mounting plate and including a slot for sliding cooperation with said guides;
   two elongated, flexible chain members attached to opposite sides of said first mounting plate and extendable toward said second mounting plate, each of said chain members including a plurality of longitudinally spaced locations for attachment of a spring; and
   two springs, one spring attached to each said guide and extending toward said first mounting plate for attachment at one of said locations on said chain members.

2. The rack of claim 1 wherein said first contact means are insulating.

3. The rack of claim 1 wherein said chain members comprise chains having a plurality of links, each link being disposed for engagement by one end of said springs.

4. The rack of claim 3 wherein one of said first contact means comprises an insulated conductor, said conductor being exposed only at the point contact of said contact means.

5. The rack of claim 4 in combination with a cylindrical test electrode of precisely known surface area mounted in one of said first contact means including a conductor and its cooperating second contact means and wherein the ratio of the exposed surface of said conductor to the precisely known surface area of said mounted electrode is not greater than 0.01.

* * * * *